(12) United States Patent
Mureddu et al.

(10) Patent No.: US 11,446,641 B2
(45) Date of Patent: Sep. 20, 2022

(54) EFFICIENT CATALYST FOR THE CONVERSION OF $CO_2$ TO METHANOL

(71) Applicant: SOTACARBO-SOCIETA TECNOLOGIE AVANZATE LOW CARBON S.P.A., Carbonia (IT)

(72) Inventors: Mauro Mureddu, Carbonia (IT); Francesca Ferrara, Carbonia (IT); Alberto Pettinau, Carbonia (IT)

(73) Assignee: SOTACARBO—SOCIETA TECHNOLOGIE AVANZATE LOW CARBON S.P.A., Carbonia (IT)

( * ) Notice: Subject to any disclaimer, the term of this patent is extended or adjusted under 35 U.S.C. 154(b) by 1 day.

(21) Appl. No.: 16/981,783

(22) PCT Filed: Feb. 7, 2019

(86) PCT No.: PCT/EP2019/053068
§ 371 (c)(1),
(2) Date: Sep. 17, 2020

(87) PCT Pub. No.: WO2019/185223
PCT Pub. Date: Oct. 3, 2019

(65) Prior Publication Data
US 2021/0114002 A1    Apr. 22, 2021

(30) Foreign Application Priority Data
Mar. 30, 2018  (IT) .......................... 102018000004130

(51) Int. Cl.
*B01J 23/80*    (2006.01)
*B01J 29/03*    (2006.01)
(Continued)

(52) U.S. Cl.
CPC .......... *B01J 23/80* (2013.01); *B01J 29/0308* (2013.01); *B01J 35/1019* (2013.01);
(Continued)

(58) Field of Classification Search
CPC .................................................... B01J 29/0308
See application file for complete search history.

(56) References Cited

U.S. PATENT DOCUMENTS

| | | | |
|---|---|---|---|
| 4,863,894 A * | 9/1989 | Chinchen | B01J 23/80 502/343 |
| 6,376,562 B1 * | 4/2002 | Ihm | B01J 35/0006 502/343 |
| 2012/0225956 A1 * | 9/2012 | Studt | B01J 23/825 977/773 |

FOREIGN PATENT DOCUMENTS

| | | |
|---|---|---|
| CN | 104001517 A | 8/2014 |
| CN | 106076395 A | 11/2016 |

(Continued)

OTHER PUBLICATIONS

Machine translation of CN 104001517A, pulication date Aug. 27, 2014.*

(Continued)

*Primary Examiner* — Jun Li
(74) *Attorney, Agent, or Firm* — Carmel Patent Agency; Robert J. Ballarini

(57) ABSTRACT

An efficient catalyst for the synthesis of methanol by catalytic hydrogenation of carbon dioxide is provided. A process for the preparation of the catalyst by self-combustion of a gel and a process for the synthesis of methanol by catalytic hydrogenation of carbon dioxide are also presented. The catalyst has the following formula $(Cu)_x(ZnO)_y(ZrO_2)_z$ supported on mesoporous silica.

18 Claims, 1 Drawing Sheet

(51) Int. Cl.
    *B01J 35/10*     (2006.01)
    *B01J 37/08*     (2006.01)
    *C07C 29/154*    (2006.01)

(52) U.S. Cl.
    CPC ....... *B01J 35/1042* (2013.01); *B01J 35/1061* (2013.01); *B01J 37/08* (2013.01); *C07C 29/154* (2013.01); *B01J 2231/625* (2013.01); *B01J 2523/17* (2013.01); *B01J 2523/27* (2013.01); *B01J 2523/48* (2013.01)

(56) References Cited

FOREIGN PATENT DOCUMENTS

| | | | | |
|---|---|---|---|---|
| CN | 106076396 A | 11/2016 | | |
| WO | WO-2004083116 A1 * | 9/2004 | .............. | B01J 23/72 |
| WO | WO-2017182893 A1 * | 10/2017 | .............. | B01J 23/80 |

OTHER PUBLICATIONS

Machine translation of CN 106076395 A, pulication date Nov. 9, 2016.*

Machine translation of Gao et al (CN106076395A), publication date Nov. 9, 2016.*

Zhao et al. (Triblock Copolymer Syntheses of Mesoporous Silica with Periodic 50 to 300 Angstrom pores, Science vol. 279: Jan. 1998, 548-552).*

\* cited by examiner

Fig.1 – A
Fig. 1 – B
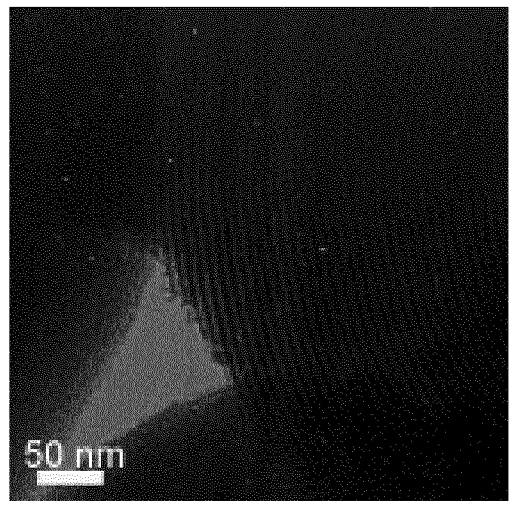
Fig.1 - C
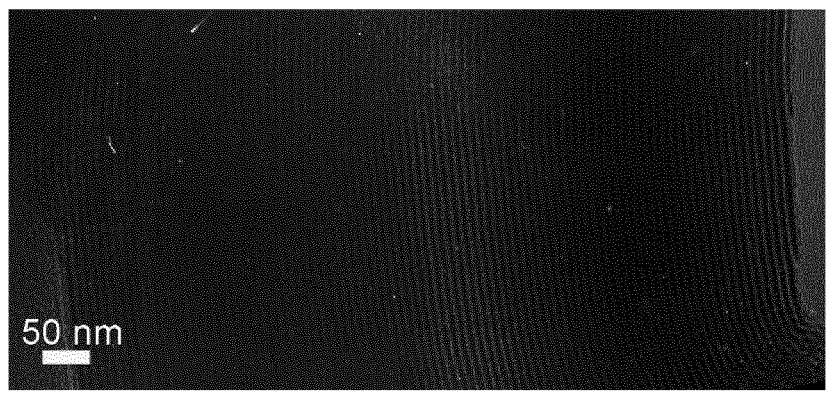
Fig. 1 – D
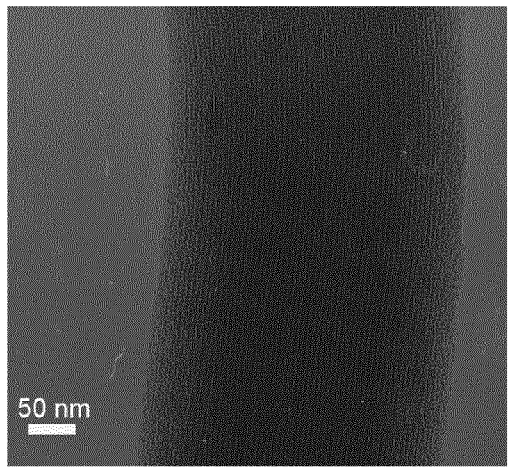
Fig. 1 - E
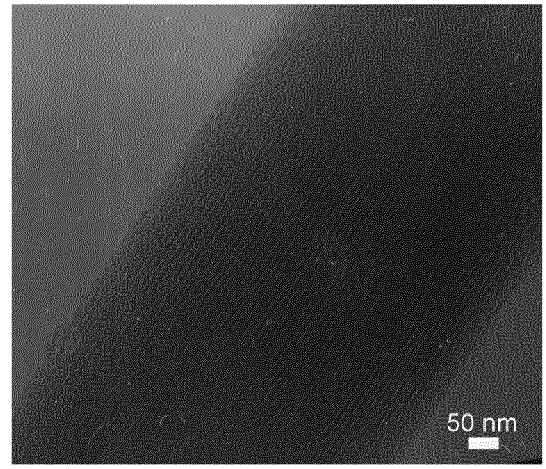

EFFICIENT CATALYST FOR THE CONVERSION OF $CO_2$ TO METHANOL

TECHNICAL FIELD

The present invention relates to efficient catalysts for the synthesis of methanol by catalytic hydrogenation of $CO_2$. Furthermore, it is also related to an innovative process for the preparation of said catalysts and to a process for the synthesis of methanol by catalytic hydrogenation of $CO_2$.

BACKGROUND ART

Due to the continuous increase in global energy demand owing to both population growth and industrial development, the concentration of carbon dioxide (hereinafter referred to as $CO_2$) in the atmosphere has reached the level of about 400 ppm in 2016; as known, $CO_2$ is considered one of the main causes of climate change. The most recent policies to stabilize and reduce $CO_2$ emissions are promoting research in the field of capture, storage, and more recently the use of $CO_2$.

One of the strategies that are gaining considerable success is the use of $CO_2$, together with the hydrogen deriving from renewable sources, as a reagent to produce methanol, which can in turn be used as an additive in gasolines or clean fuel, or converted into other chemicals (olefins for example). One of the main problems related to the exploitation of this technology is to be able to prepare an active and selective catalyst capable of activating the stable $CO_2$ molecule and converting it into methanol through catalytic hydrogenation. To this end, in recent years many studies have been conducted and published on catalytic systems for the catalysis of the hydrogenation of $CO_2$ to give methanol; however, as shown in Table 5 of Example 10, which summarizes many of the recent publications, the efficiency of the developed catalysts is still low.

In a very recent publication, Tursunov et al. in Journal of the Taiwan Institute of Chemical Engineers, vol. 78, pag. 416-422, (2017), describes catalytic systems based on CuO/ZnO supported on aluminum oxides ($Al_2O_3$) and silicon oxide ($SiO_2$) for the synthesis of methanol by catalytic reduction of $CO_2$. In particular, the CuO—ZnO/$A_2O_3$ and CuO—ZnO/$SiO_2$ catalysts have been prepared by impregnation and precipitation of metals over the supports. The CuO—ZnO/$Al_2O_3$ catalyst has proved to be the most selective and active to give methanol. No information is given about the silica (hereinafter referred to as $SiO_2$) used as a support if not the BET surface area data equal to 191 m²/g, from which it can be understood that it was merely traditional porous silica, in fact the two CuO—ZnO/$SiO_2$ catalysts prepared from such silica showed a BET surface area value of 131 and 133 m²/g.

The catalytic efficiency and the performance of the catalysts prepared by Tursunov at al. strongly depend on pressure and, above all, temperature, with the best results at 270° C. In particular, higher temperatures, i.e. 270° C. instead of 250° C., and/or higher pressures, i.e. 50 bar instead of 30 bar, lead to higher methanol productivity, as can easily be deduced from the following summary Table 1, taken from this article, for catalysts both supported on alumina ($Al_2O_3$) and those supported on silica ($SiO_2$).

TABLE 1

| | | STY (MeOH) (g/gcat/h) | | | |
| | | Conditions (T - P) (° C., bar) | | | |
| n. | Catalyst | 250 - 30 | 250 - 50 | 270 - 30 | 270 - 50 |
| --- | --- | --- | --- | --- | --- |
| 1 | CuO—ZnO/$Al_2O_3$ (i) | 0.10 | 0.15 | 0.21 | 0.28 |
| 2 | CuO—ZnO/$Al_2O_3$ (p) | 0.06 | 0.11 | 0.14 | 0.19 |
| 4 | CuO—ZnO/$SiO_2$ (i) | 0.06 | 0.07 | 0.09 | 0.12 |
| 5 | CuO—ZnO/$SiO_2$ (p) | 0.045 | 0.05 | 0.08 | 0.09 |

The best operating conditions are at 270° C. and 50 bar, with productivity in terms of methanol about three times for the catalysts supported on alumina and about twice for those supported on silica, compared to the productivity obtained at 250° C. and 30 bar.

The CuO—ZnO/$Al_2O_3$ (i) catalyst gave the best results with a methanol STY of 0.28 (g/g cat/h) at 270° C. and 50 bar (i.e. 5.0 MPa). Moreover at 270° C. and 50 bar, the CuO—ZnO/$Al_2O_3$ catalyst shows a productivity in terms of methanol STY about twice that obtained under the same conditions with the CuO—ZnO/$SiO_2$ catalyst (i, p) equal to 0.12 and 0.09 (g/g cat/h). Tursunov states that all catalysts have shown a decreased methanol productivity (STY) reducing the temperature to 250° C. Furthermore, he concludes that the CuO—ZnO/$Al_2O_3$ (i) catalyst has shown the highest catalytic activity for the hydrogenation of $CO_2$ to methanol, with the highest and best methanol STY reached equal to 0.28 (g/g cat/h) at 270° C. and 50 bar, remembering however that it is only 0.10 (g/g cat/h) at 250° C. and 30 bar.

The publication CN104001517A discloses a catalyst based on Copper oxide (CuO), Zinc oxide and Zirconium oxide, as evident by FIG. 2 of said document, supported over mesoporous silica and prepared according to a traditional impregnation process. Said catalysts show surface area of 217.9 m²/g, 198.8 m²/g and 207.3 m²/g and pore volume from 0.236 to 0.36 cm³/g.

The publication CN106076395A discloses catalysts based on Copper, Zinc oxide and Zirconium oxide, supported over $NH_2$— functionalized SBA-15 mesoporous silica. They are prepared by a process that firstly reduces copper ions to metallic copper over the silica surface and then adding Zinc oxide and Zirconium dioxide by a traditional impregnation process. Said catalysts show Copper surface area comprised between 16.7 and 30.2 m²/g and Copper dispersion from 11.7% to 22.9% (see table 1). These functionalized silica catalysts provide methanol productivity ranging from 1.25 to 4.58 ($Y_{CH3OH}$ (%)) and selectivity comprised between 8.3% to 18.3% ($S_{CHOH3}$(%)) (see table 2).

Finally, the publication CN106076396A discloses catalysts based on Copper, Zinc oxide, Zirconium oxide and doped with Gold, supported over $NH_2$— functionalized SBA-15 mesoporous silica. FIG. 4 shows the selectivity of these catalysts which is comprised between about 7% to about 11.5% ($S_{CH3OH}$ (%)).

SUMMARY OF INVENTION

The problem addressed by the present invention is therefore that of providing a better catalyst, that is to say more efficient (more productive and/or selective) for the preparation of methanol by catalytic hydrogenation of $CO_2$. Furthermore, as an additional problem, it would be desirable to have efficient catalysts at less favorable operating conditions, i.e. at 250° C. and 30 bar instead of 270° C. and as much as 50 bar.

Finally, an additional problem is the development of a process which allows to obtain a high-performance catalyst, which, further, does not need to be activated in a reducing atmosphere, by means of a delicate activation procedure, which is a major drawback reported for the known catalysts.

This problem is solved by the catalyst of the present invention and by the process for its preparation, as delineated by the appended claims, whose definitions are an integral part of the present description.

In particular, the invention relates to an advanced nanocomposite catalyst of the "supported" type comprising copper, zinc oxide or copper, zinc oxide and zirconium dioxide, confined to a mesoporous silica.

Another aspect is an innovative process for preparing said catalyst.

Another object is the process for the preparation of methanol by catalytic hydrogenation catalyzed by the catalyst of the invention.

Further characteristics and benefits of the catalysts of the invention and of the process for their preparation will be apparent from the description of the exemplary embodiments of the invention.

DESCRIPTION OF THE FIGURES

FIGS. 1-A, 1-B and 1-C show images of the catalyst of the invention CZZS_20_1, i.e. of Cu/ZnO/ZrO$_2$@SBA-15 with a Cu/ZnO ratio of 1.0 and 20% metal load on the silica, acquired with TEM microscopy (transmission electron microscopy) with a Jeol 200CX microscope operating at an accelerating voltage of 200 kV.

FIGS. 1-D and 1-E show TEM images of the catalyst CZZS_35_2.5, i.e. of Cu/ZnO/ZrO$_2$@SBA-15 with a Cu/ZnO ratio of 2.5 and 35% metal loading on the silica.

DESCRIPTION OF EMBODIMENTS

An object of the present invention is a catalyst for the preparation of methanol by catalytic hydrogenation of the carbon dioxide comprising copper and zinc oxide or copper, zinc oxide and zirconium dioxide, and is supported on a support consisting of mesoporous silica.

According to a preferred embodiment, indeed, the catalyst of the invention comprises copper, zinc oxide and zirconium dioxide, and is supported on mesoporous silica.

The support consisting of mesoporous silica means that the support is constituted only by mesoporous silica, i.e. only by silica. Thus, the mesoporous support does not include any functionalized mesoporous silica, with any functional group. In other words, the mesoporous silica of the catalyst of the invention is unfunctionalized mesoporous silica.

Copper is metal copper of formula Cu or Cu (0) or Cu$^0$, zinc oxide has the chemical formula ZnO and zirconium dioxide has the chemical formula ZrO$_2$.

The catalyst for the preparation of methanol by catalytic hydrogenation of the carbon dioxide comprises the following composition (I):

$$(Cu)x(ZnO)y(ZrO_2)z \quad (I)$$

wherein x is comprised between 0.3 and 0.8, y is comprised between 0.1 and 0.5, z is comprised between 0.0 and 0.4; which is supported on a support consisting of mesoporous silica.

The values of x, y, and z express the content of each constituent in terms of relative molar equivalents, i.e. it is the ratio between the moles of the constituent and the total moles of the other constituents of the composition, intended only as a composition of metals and metal oxides, therefore excluding the inert siliceous support.

Indeed, it has been surprisingly found an efficient nanocomposite catalyst of the supported type comprising copper (metal), zinc oxide or, copper (metal), zinc oxide and zirconium dioxide, confined to a mesoporous silica for the specific application of catalytic hydrogenation of CO$_2$ for the production of methanol.

According to a more preferred embodiment, the catalyst comprises copper and zinc oxide or copper, zinc oxide and zirconium dioxide, and is supported on mesoporous silica of the SBA-15 type.

According to an even more preferred embodiment, the catalyst comprises copper, zinc oxide and zirconium dioxide, and is supported on mesoporous silica of the SBA-15 type.

Many solids which can be used as catalytic supports, for example zeolites, alumina, silica, etc., are known today, as well as many and many types of silica are known. In particular, among the various types of silica there are those with a mesoporous or mesostructured structure which therefore have pores having a diameter in the order of nanometers (abbreviated nm).

According to the International Union of Pure and Applied Chemistry (IUPAC), a material is called microporous if the pore diameter is less than 2 nm, is called mesoporous if the pore diameter is between 2 and 50 nm and is called macroporous if the pore diameter is greater than 50 nm.

Among the various mesostructured silicas, the mesoporous silica i.e., the silica having pore diameters between 2 and 50 nm, was found to be that which, in combination with copper, zinc oxide or copper, zinc oxide and zirconium dioxide, gives an efficient catalyst for the synthesis of methanol by catalytic hydrogenation of CO$_2$.

Mesoporous silica is a porous mesostructured material, i.e. it has mesoporous structure, known since the late '70s and to date are known different types of mesoporous silica of which we give a brief mention:

mesoporous silica MCM-41 having two-dimensional hexagonal crystallographic structure and spatial group P6 mm, mesoporous silica MCM-48 having cubic structure and La3d spatial group, mesoporous silica MCF (mesostructured cellular foam), also known as mesostructured silica, SBA-type mesoporous silica (abbreviation of Santa Barbara Amorphous) which includes the SBA-15 (hexagonal), SBA-16 (cubic), and others.

In general, the different types of mesoporous silica, including those just mentioned, differ in particle morphology (for example, discs, spheres, powders, etc.) and for pore geometries.

There is also a mesoporous silica functionalized with thiol groups (—SH) or aminic groups (—NH$_2$), but said silica is excluded from the mesoporous silica constituting the catalyst of the present invention, as said above.

The pores of mesoporous silica may have a specific geometry, for example they may have hexagonal geometry, cubic geometry, cylindrical geometry, etc.

Mesoporous silica whose pores have hexagonal geometry is called hexagonal mesoporous silica. The hexagonal mesoporous silica, is preferred for the catalyst of the invention.

A type of hexagonal mesoporous silica is known by the name of SBA-15; SBA-15 is particularly preferred as a support for the catalyst of the invention.

Mesoporous silica whose pores have cubic geometry is called cubic mesoporous silica. A type of cubic mesoporous silica is known as SBA-16.

In other words, the hexagonal mesoporous silica consists of silica having hexagonal mesoscopic organization. These pores are presented as channels with a hexagonal symmetry, arranged parallel to each other. The mesoporous silica is therefore made up of parallel beams and/or pore planes with specific geometry.

Mesoporous silica, and in particular hexagonal mesoporous silica of the SBA-15 type, was prepared for the first time, characterized and described by Dongyuan Zhao et al. in Science 279, 548-552, (1998), at the University of California, Santa Barbara, hence the abbreviated name of the product. Zhao prepares and describes hexagonal mesoporous silica SBA-15, with a pore diameter of 5 to 30 nm.

Zhao et al. defines the mesoporous SBA-15 silica as constituted by well-ordered hexagonal and mesoporous and amorphous silica structures with uniform pore size. The SBA-15 has a two-dimensional hexagonal pore structure.

The mesoporous silica SBA-15 has a two-dimensional hexagonal structure belonging to the P6 mm space group. This structure is highly ordered.

The pore size of the mesoporous silica of the present catalyst is comprised from 2 to 50 nm; preferably it is comprised between 2 and 30 nm, more preferably the pore size is comprised from 5 to 30 nm, even more preferably, it is comprised between 6 and 9 nm, and finally, the best is comprised from 6 to 7 nm, or is 6.7 nm.

The catalyst in which the mesoporous silica has hexagonal geometry, is amorphous silica, and the pore diameter is comprised between 5 and 30 nm is preferred. This mesoporous silica corresponds to that prepared by Zhao et al. in the aforementioned article.

The catalyst in which the mesoporous silica has hexagonal geometry, is amorphous silica, and the pore diameter is comprised between 5 and 10 nm is more preferred, and wherein the pores diameter is comprised between 6 nm and 9 nm is even more preferred.

The pore volume of mesoporous silica is comprised between 0.7 and 1.4 cm$^3$/g, preferably between 1.0 and 1.4 cm$^3$/g, more preferably between 1.10 and 1.30 cm$^3$/g.

Unlike traditional porous silica, mesoporous silica has very high surface area values. In particular, the Brunauer-Emmett-Teller (BET) surface area of mesoporous silica is comprised between 500 m$^2$/g and 1100 m$^2$/g, preferably between 500 m$^2$/g and 800 m$^2$/g, even more preferably between 650 m$^2$/g and 750 m$^2$/g.

According to a preferred embodiment of the invention the hexagonal mesoporous silica has a pore size comprised between 5 nm and 30 nm, pore volume comprised between 1.0 cm$^3$/g and 1.4 cm$^3$/g and a surface area comprised between 500 m$^2$/g and 800 m$^2$/g.

According to an embodiment of the most preferred invention, the hexagonal mesoporous silica has a pore size comprised between 6 and 9 nm, pore volume comprised between 1.10 cm$^3$/g and 1.30 cm$^3$/g and a surface area comprised between 500 m$^2$/g and 800 m$^2$/g.

The catalyst comprises Cu and ZnO, or, Cu, ZnO and ZrO$_2$ and mesoporous silica. The ratio between the sum of the weight of Cu and ZnO, or the weight of Cu, ZnO and ZrO$_2$, and the weight of the mesostructured silica is comprised between 10% and 50% (% weight/weight), preferably is comprised between 15% and 40% or between 15% and 30%, more preferably is comprised between 15% and 25% (w/w %) or is 20% because it provides the best conversions of CO$_2$ to methanol (see entry from 2 to 4 of Table 4 of Example 8, in particular the comparison between entries 2 and 4).

The support for the catalyst of the invention, i.e. mesoporous silica SBA-15, can be conveniently prepared and characterized according to the teachings of Dongyuan Zhao et al. in Science 279, p. 548-552, (1998), or according to the two preparations of Example 2 reported in the experimental section. Alternatively, mesoporous silica, having various geometries (cubic, hexagonal, lamellar, cc.) and various pore sizes is commercially available from Aldrich (USA). Also, the mesoporous silica SBA-15 is commercially available for example from Aldrich (USA).

The catalyst for the preparation of methanol by catalytic hydrogenation of the carbon dioxide, in addition to the mesoporous silica, it comprises the following composition (I):

$$(Cu)x(ZnO)y(ZrO_2)z \qquad (I)$$

wherein x is comprised between 0.3 and 0.8, y is comprised between 0.1 and 0.6, z is comprised between 0.0 and 0.4.

The value of x, which expresses the metallic copper content in terms of relative molar equivalents, i.e. copper moles divided by the sum of the moles of copper and oxides of zinc and zirconium, if the latter is present, is comprised between 0.3 and 0.8, preferably it is between 0.3 and 0.6 and even more preferably between 0.4 and 0.5.

The value of y, which expresses the zinc oxide content in terms of relative molar equivalents, is comprised between 0.1 and 0.6, preferably between 0.1 and 0.4, and even more preferably between 0.2 and 0.3.

The value of z, which expresses the, optional, content of zirconium dioxide in terms of relative molar equivalents, is comprised between 0.0 and 0.4, where when z is 0.0 the catalyst does not contain zirconium dioxide, preferably z is comprised between 0.2 and 0.4, and even more preferably it is 0.3.

According to a more preferred embodiment of the invention, the catalyst has the following composition (I):

$$(Cu)x(ZnO)y(ZrO_2)z \qquad (I)$$

wherein x is comprised between 0.3 and 0.6, y is comprised between 0.1 and 0.4, and z is comprised between 0.2 and 0.4 and the mesoporous silica.

According to a more preferred embodiment of the invention x is comprised between 0.3 and 0.6, y is between 0.1 and 0.4 and z is between 0.2 and 0.4 and the ratio of the sum of the weight of Cu, ZnO and ZrO$_2$, and the weight of the mesostructured silica it is comprised between 15 and 25%.

According to a more preferred embodiment of the invention, the catalyst comprises the composition (I) in which x is comprised between 0.4 and 0.5, y is comprised between 0.2 and 0.3 and z is comprised between 0.2 and 0.4.

According to an even more preferred embodiment of the invention, the catalyst comprises the composition (I) in which x is comprised between 0.4 and 0.5, y is comprised between 0.2 and 0.3 and z is comprised between 0.2 and 0.4 and the ratio between the sum of the weight of Cu, ZnO and ZrO$_2$, and the weight of the mesostructured silica is comprised between 15 and 40%, more preferably it is comprised between 15% and 25%.

Again, according to an even more preferred embodiment of the invention, the catalyst comprises the composition (I) in which x is comprised between 0.4 and 0.5, y is comprised between 0.2 and 0.3 and z is 0.3 and the ratio between the sum of Cu, ZnO and $ZrO_2$, and the weight of the mesostructured silica is comprised between 15% and 25%.

According to an even more preferred embodiment of the invention, the catalyst comprises the mesoporous silica and the composition (I) wherein x is 0.5, y is 0.2 and z is 0.3 or wherein x is 0.4, y is 0.3 and z is 0.3.

According to an increasingly preferred embodiment of the invention, the catalyst comprises the mesoporous silica and the composition (I) wherein x is 0.5, y is 0.2 and z is 0.3 or where x is 0.4, y is 0.3 and z is 0.3 and the ratio of the sum of the weights of Cu, ZnO and $ZrO_2$, and the weight of the mesostructured silica is comprised between 15 and 25%.

According to the most preferred embodiment, the catalyst comprises the mesoporous silica and the composition (I) wherein x is 0.5, y is 0.2 and z is 0.3 or where x is 0.4, y is 0.3 and z is 0.3 and the ratio of the sum of the weights of Cu, ZnO and $ZrO_2$, and the weight of the mesostructured silica is equal to 20%. Said catalyst is the one which provides the best conversions of $CO_2$ to methanol as shown in Table 4 of experiment 8, entry 2 and 3.

The catalyst, in addition to the aforesaid composition (I) where x is comprised between 0.3 and 0.8, y is comprised between 0.1 and 0.6, z is comprised between 0.0 and 0.4, and in addition to the mesoporous silica, it can further comprise copper oxide (CuO). Preferably, the amount of copper oxide is such that, added to the amount of (metallic) copper, it provides the value of x.

According to a more preferred embodiment of the invention, the catalyst consists of the following composition (I):

$$(Cu)x(ZnO)y(ZrO_2)z \qquad (I)$$

wherein x is comprised between 0.3 and 0.6, y is comprised between 0.1 and 0.4 and z is comprised between 0.2 and 0.4, where the sum of x+y+z is equal to 1.0, and is supported over a support constituted by the mesoporous silica. It therefore does not include other constituents.

According to a more preferred embodiment of the invention x is comprised between 0.3 and 0.6, y is comprised between 0.1 and 0.4 and z is comprised between 0.2 and 0.4, where the sum of x+y+z is equal to 1.0, and the ratio of the sum of the weights of Cu, ZnO and $ZrO_2$, and the weight of the mesostructured silica is comprised between 15 and 25%.

According to a more preferred embodiment of the invention x is comprised between 0.4 and 0.5, y is comprised between 0.2 and 0.3 and z is comprised between 0.2 and 0.4, where the sum of x+y+z is equal to 1.0.

According to an even more preferred embodiment of the invention x is comprised between 0.4 and 0.5, y is comprised between 0.2 and 0.3 and z is comprised between 0.2 and 0.4, preferably z is 0.3, where the sum of x+y+z is equal to 1.0, and the ratio of the sum of the weights of Cu, ZnO and $ZrO_2$, and the weight of the mesostructured silica is comprised between 15 and 25%. This catalyst, which does not therefore includes other components, is the one that provides the highest productivity in terms of methanol as shown in Table 4 of Example 8, entry 2 and 3.

The catalyst in which z is different from zero is preferred because it is a catalyst which provides the highest productivity in terms of methanol (see Table 4 of Example 8, entries 2-4 versus entry 5).

In particular, according to a preferred embodiment, the catalyst of formula (I) has a value of z comprised between 0.2 and 0.4, even more preferably it is equal to 0.3. The presence of zirconia (zirconium dioxide) in these quantities improves the catalytic efficiency of the catalyst in terms of methanol produced, as shown in Table 2, where, with the same support and composition of copper and zinc oxide, the catalysts containing said amounts of zirconia provide the highest productivity in terms of methanol.

According to a preferred embodiment, the catalyst having composition (I) has a value of the ratio x/y is comprised between 0.9 and 3.0, preferably between 0.9 and 2.6, still more preferably between 0.9 and 1.1, or between 1.2 and 1.4, or between 2.4 and 2.6.

The catalysts of the present invention, as illustrated in Table 5 of Example 10, have proved particularly efficient in catalyzing the catalytic hydrogenation of $CO_2$ to give methanol, both in absolute terms and in relative terms, at parity of metal composition and operating conditions, with known catalysts.

In particular, the catalyst of the invention allows to reach productivity STY values (i.e. Space Time Yield which means the amounts of methanol yield produced per gram of catalyst per hour ($g_{CH3OH} g_{cat}^{-1} h^{-1}$)) comprised in the range from 150 to 450 mg $CH_3OH$ $h^{-1}$ $g_{cat}^{-1}$, i.e. values of $Y_{CH3OH}$ (%) comprised from 2.45% to 7.0%.

More in particular, the catalyst of the invention also comprising zirconium dioxide allows to reach higher productivity with STY values comprised in the range from 250 to 450 mg $CH_3OH$ $h^{-1}$ $g_{cat}^{-1}$, i.e. values of $Y_{CH3OH}$ comprised from 3.9% to 7.0% (see Table 4 and Table 6).

Again more in particularly, the catalyst of the invention wherein the ratio between the sum of the weight of Cu, ZnO and $ZrO_2$, and the weight of the mesostructured silica is comprised between 15% and 25%, shows the highest productivity with STY values comprised in the range from 320 to 450 mg $CH_3OH$ $h^{-1}$ $g_{cat}^{-1}$, i.e. values of $Y_{CH3OH}$ comprised from 5.0% to 7.0% (see entry 2 and 3 of Table 4 and Table 6).

Moreover, unlike the prior art catalysts, those of the invention do not need to operate at more extreme conditions, i.e. at 270° C. and 50 bar, already providing excellent performances, at 250° C. and 30 bar, with production of methanol even higher than 300 mg $CH_3OH$ $h^{-1}$ $g_{cat}^{-1}$, i.e. productivity never reached until today, to the knowledge of the Applicant.

Another very important aspect of the catalysts of the invention is the extraordinary selectivity toward to methanol. Indeed, the selectivity $S_{CH3OH}$ expressed in mol. % is comprised between 24% and 36% (see table 4 and Table 6), which is higher compared to that of the catalysts of above mentioned prior art, especially the last two mentioned documents.

More in particularly, the catalyst of the invention wherein the ratio between the sum of the weight of Cu, ZnO and $ZrO_2$, and the weight of the mesostructured silica is comprised between 15% and 25%, show the highest selectivity $S_{CH3OH}$ values comprised in the range from 26% to 36% (mol. %) (see entry 2, 3 and 5 of Table 4 and Table 6).

Another very important advantage offered by the catalysts of the invention is that, unlike those known to date, they do not require the delicate activation step. This peculiarity of the catalysts of the invention derives from the particular process with which they are prepared.

The above-mentioned catalysts, including all their features, as above described, can be prepared according the process described hereafter.

As with most industrial catalysts, the preparation method has considerable influence on the final performances of the catalyst.

The known methods for the preparation of metal oxides supported by nanoparticles involve the deposition of a precursor metal from a liquid phase onto a preformed support by different deposition techniques through precipitation procedures. However, these conventional methods result in the deposition of a large part of the metallic precursor into the outer portions of the support bodies thus obtaining a heterogeneous material which shows an "egg-shell" distribution and which can lead to inhomogeneous distribution after drying.

Therefore a very important aspect is the process for the preparation of the catalyst for the preparation of methanol by catalytic hydrogenation of the carbon dioxide comprising:
copper and zinc oxide, or
copper, zinc oxide and zirconium dioxide;
which is supported on a support consisting of mesoporous silica; said process comprises the following steps:
a) preparation of the aqueous solution comprising a complexing agent and a salt of copper and one of zinc or, a copper salt, one of zinc and one of zirconium;
b) mixing of the mesoporous silica support with the solution of step a);
c) optional, sonication treatment of the mixture of step b);
d) formation of the gel;
e) trigger the self-combustive process of the gel and self-combustive step;
f) obtainment of the catalyst.

Indeed, it has been surprisingly found that this process, allowing the solution of step a) to enter into the pores of the silica, at the end of the self-combustion phase, provides a homogeneous dispersion of the active catalytic phase consisting of metals and metal oxides inside the silica channels, and not only outside it, thus giving rise to a catalyst with a very large surface area, a very large Copper surface area, high Copper dispersion, high pore volume; all features that are responsible of the excellent catalytic performance in converting the $CO_2$ to methanol, both in terms of methanol productivity and methanol selectivity, as said above.

The catalyst of the invention, has indeed high values of surface area, measured according BET (Brunauer-Emmett-Teller) (abbreviate as $S_{BET}$), comprised in the range from 300 m$^2$/g to 500 m$^2$/g, as measured according to BET method from the adsorption data (Brunauer, S., P. H. Emmett, and E. Teller. 1938. Adsorption of gases in multimolecular layers. Journal of the American Chemical Society 60(2): 309-319. doi: 10.1021/ja01269a023). The surface area is indeed determined by physical adsorption of a gas on the surface of the solid and by calculating the amount of adsorbate gas corresponding to a monomolecular layer on the surface. The determination is carried out at the temperature of liquid nitrogen (−196° C.).

More particularly the catalyst has high values of surface area $S_{BET}$ comprised in the range from 400 m$^2$/g to 480 m$^2$/g (see entries 2, 3 and 4 of Table 3 in Example 7). Even more particularly the catalyst has high values of surface area $S_{BET}$ comprised in the range from 430 m$^2$/g to 450 m$^2$/g (see entries 2, 3 and 4 of Table 3 in Example 7).

This high surface area comprised in the range from 300 m$^2$/g to 500 m$^2$/g is responsible of the high productivity in term of methanol STY whose values are comprised in the range from 150 to 450 mg CH$_3$OH h$^{-1}$ g$_{cat}^{-1}$, i.e. values of $Y_{CH3OH}$ (%) comprised from 2.45% to 7.0% (see table 4 of example 6).

More in particular, the catalyst of the invention also comprising zirconium dioxide, i.e. wherein z is comprised between 0.2 and 0.4, allows to reach higher productivity STY values comprised in the range from 250 to 450 mg CH$_3$OH h$^{-1}$ g$_{cat}^{-1}$, i.e. values of $Y_{CH3OH}$ comprised from 3.9% to 7.0% (see Table 4 and Table 6). In particular this catalyst has values of surface area $S_{BET}$ comprised in the range from 300 m$^2$/g to 480 m$^2$/g (see entries 2, 3 and 4 of Table 4 in Example 8).

Again more in particular, the catalyst of the invention also comprising zirconium dioxide, i.e. wherein z is comprised between 0.2 and 0.4, and having values of surface area $S_{BET}$ comprised in the range from 430 m$^2$/g to 450 m$^2$/g (see entries 2 and 3 of Table 4 in Example 8) allows to reach higher productivity STY values comprised in the range from 320 to 450 mg CH$_3$OH h$^{-1}$ g$_{cat}^{-1}$, i.e. values of $Y_{CH3OH}$ comprised from 5.0% to 7.0% (see entry 2 and 3 of Table 4 and Table 6).

Again more in particularly, the catalyst of the invention wherein the ratio between the sum of the weight of Cu, ZnO and ZrO$_2$, and the weight of the mesostructured silica is comprised between 15% and 25%, show the highest productivity STY values comprised in the range from 320 to 450 mg CH$_3$OH h$^{-1}$ g$_{cat}^{-1}$, i.e. values of $Y_{CH3OH}$ comprised from 5.0% to 7.0% (see entry 2 and 3 of Table 4 and Table 6).

The catalyst has a Copper surface area comprised between 100 and 400 m$^2$ of Copper (0) per gram of Copper, wherein Copper (0) means metallic Copper (see example 11). Preferably, the catalyst has Copper surface area comprised between 150 and 350 m$^2$/g. Also this feature of the catalyst is responsible of the productivity and/or selectivity of the catalyst.

The catalyst has Copper dispersion comprised between 25% and 50%, preferably comprised between 40% and 50% (see example 11). Also this feature of the catalyst is responsible of the productivity and/or selectivity of the catalyst. Indeed, the process of the invention allows a higher distribution of copper, i.e. between 25% and 50% (as measured in example 11) which effects the productivity and/or selectivity of the catalyst.

The catalyst has a pore volume comprised between 0.5 cm$^3$/g and 0.9 cm$^3$/g, preferably comprised between 0.7 cm$^3$/g and 0.9 cm$^3$/g. (see table 3 in exp. 7). In addition, this feature of the catalyst can be responsible of the productivity and/or selectivity of the catalyst.

The catalyst can have a pore diameter comprised between 6.2 and 6.5 nm, preferably comprised between 6.4 and 6.5 nm. The pore diameter has been calculated with the BJH method, i.e. Barrett, Joyner, Halenda method (see paragraph [00136] and see example 7).

The process above described provides the catalyst for the preparation of methanol by means of catalytic hydrogenation of the carbon dioxide having any one or more of the features described in the all previous pages, in the claims and in the examples.

Step a) can conveniently be carried out by first preparing an aqueous solution comprising the copper and zinc salts or the salts of copper, zinc and zirconium, and then, adding to said solution an aqueous solution containing the complexing agent. Or, step a) can be carried out by dissolving the copper and zinc salts or the salts of copper, zinc and zirconium in water, and, simultaneously, the complexing agent.

The complexing agent is a chemical substance able to form chemical complexes with metallic cations. In other words, complexing agent forms coordinate bonds with a metal atoms.

The complexing agent may, thus, be citric acid, glycine, urea, or others known to be able to form complex with metallic cations.

The amount of complexing agent used is comprised between 1.1 and 1.7 molar equivalents compared with the sum of the moles of the metals used, i.e. the ratio between the moles of complexing agent and the sum of the moles of the metals, i.e. moles of copper and zinc or copper, zinc and zirconium, is comprised between 1.1. and 1.7. Preferably, the amount of complexing agent used is comprised between 1.4 and 1.5 molar equivalents, even more preferably it is equal to 1.44 molar equivalents.

The solution of step a) is conveniently stirred for 30 minutes at room temperature. The solution of step a) therefore contains a complex which is formed by complexing the metals with the complexing agent.

In step b) the mesoporous silica support is mixed, i.e. impregnated, with the solution of step a), i.e. in the step b) the solution of the step a) soaks both the external surface of the mesoporous silica as well as the its porous. Step b) can be carried out by adding the solution prepared in step a) to the mesoporous silica, preferably the addition is carried out under vigorous stirring (e.g., 700 rpm) at ambient temperature. A blue dispersion is obtained with a pH of about 2.5. At the end of step b) the complex created between metals and complexing agent of the solution of step a) is also found within the pores of mesoporous silica as well as on its external surface.

The optional step c) can be carried out by sonicating the mixture prepared in step b) for 2-3 minutes. This step c) further promotes the dispersion and homogenization of the solution of step a) along the whole volume of silica. Step d) of gel formation is carried out by slow evaporation of the water. Step d) can be carried out by heating the mixture of step b) or c) at a temperature comprised between 100° C. to 150° C., preferably comprised between 100° C. and 120° C., preferably at atmospheric pressure. Step d) can be carried out in a time between 60 and 90 minutes. Preferably, step d) is carried out at a temperature comprised between 100° C. to 150° C. in a time between 60 and 90 minutes. At the end of step d) of the water evaporation a blue gel is collected.

The gel formed in the step d) is a gel or sol-gel or a pseudo-gel. In other words it is a solid jelly-like material.

Step e) can be carried out by subjecting the gel obtained in step d) to a rapid increase in temperature, preferably in a range between 270° C. to 330° C., preferably at 300° C. Step e) can be conducted by placing the gel in static air; step e) is conducted by placing the gel in an oven. Step e) can be preferably conducted by calcinaton in static air. In the step e), the temperature of 300° C. is maintained for a time between 60 and 90 minutes. During this time there is the ignition between the complexing agent and the metal salts, preferably metal nitrate salts, with decomposition of the salts.

In the step e), the triggering the self-combustive process of the gel is indeed carried out by heating the gel, preferably in a range of temperature between 270° C. to 330° C. After the self-combustive process is started, the self-combustive step is carried out simply maintaining the substrate at constant temperature, preferably in a range of temperature between 270° C. to 330° C.

At the end of step e) the product is obtained, preferably, by cooling to room temperature.

In the step f) the catalyst is obtained, e.g. by discharging of the oven.

The copper, zinc or zirconium salt of step a) can be selected from organic or inorganic salt, for example it can be nitrate, acetate, chloride, acetoacetonate, etc.

According to a preferred embodiment, the salts of copper and zinc salts or the salts of copper, zinc and zirconium are the respective nitrate salts.

The complexing agent of step a) plays two important roles; on one side it is the fuel of the combustion reaction and on the other side it forms complexes with metal ions, complexes which avoid the precipitation of hydroxylated compounds.

According to a preferred embodiment, the complexing agent may be citric acid, glycine, urea.

According to a more preferred embodiment of said process, the complexing agent is glycine. Indeed, glycine provides catalysts having smaller particles and catalysts having greater surface area.

The amount of glycine used is comprised between 1.1 to 1.7 molar equivalents compared to the sum of the moles of the metals used, i.e. the ratio between the moles of glycine and the sum of the moles of the metals. Preferably, the amount of glycine used is comprised between 1.4 and 1.5 molar equivalents, even more preferably it is 1.44 molar equivalents.

According to one more preferred embodiment the salts of copper and zinc salts or the salts of copper, zinc and zirconium are the respective nitrate salts and the complexing agent is glycine. Glycine forms with the nitrated counterions a particular complex which has the advantage that when it is heated in a hot furnace, it burns at relatively low temperatures, lower than other metal complexes, through a self-propagating process (in situ auto-combustion) by rapidly converting the mixtures of precursors directly in the products. Glycine is the fuel of said self-ignition reaction and the nitrate ion constitutes the oxidizer.

According to a more preferred embodiment of the aforesaid process, in step b) the mesoporous silica is of the SBA-15 type.

The catalyst obtainable from this process has the composition and the features already described in the previous pages.

It has been surprisingly found that the catalyst for the preparation of methanol by catalytic hydrogenation of the carbon dioxide obtainable from said process, unlike the known catalysts, does not require the delicate activation step thereof to operate.

The aforementioned process of preparing the catalyst for the hydrogenation of methanol $CO_2$ provides the following advantages:

(i) improve the dispersion of the active phase in the hydrogenation process resulting in improved catalytic performance when compared with the most recent data reported in the literature (see high surface area values);

(ii) to get in phase of calcination in static air, i.e. in the step e), the active phase of copper already in the metallic state, contrary to the obtaining of the active phases based on copper oxide of the most common catalysts of manufacturing processes; this allowed to by-pass, with all the benefits in economic, engineering and chemical terms, the in situ activation treatment for obtaining the copper metallic phase, obligatorily required by all catalyst producers to make the material active and be able to effectively perform their task. This process has therefore enabled an active phase to be obtained with characteristics different from those normally deriving from conventional impregnation or different from those obtained in a simple self-combustion sol-gel, allowing confinement and dispersion of the active phase on the mesoporous silica support, both externally and internally to the mesopores of silica as shown in FIG. 1.

The catalyst obtainable from said process, used in the production process of methanol from $CO_2$, had the triple result of: (i) improving, through the confinement and use of mesoporous silica, the ability of the catalyst to interact with $H_2$ and $CO_2$ increasing the final catalytic performance of the material and greatly limit the common sintering phenomena occurring in "conventional" catalysts; (ii) obtain, through the innovative impregnation procedure with sol-gel approach of self-combustion, already the active phase of metal copper for the $CO_2$ hydrogenation reaction without any further activation treatment which is indispensably required by all known commercially available catalysts; (iii) for the first time a binary catalytic system (Cu/ZnO) or ternary (Cu/ZnO/$ZrO_2$) confined within the mesopores of the mesostructured silica, in particular the SBA-15 through the innovative impregnation approach with sol-gel of self-combustion. The catalyst obtained from this process is used without any reductive activation treatment for the catalytic hydrogenation of sole $CO_2$ for the production of methanol.

In the literature, catalysts based on copper oxide (CuO) are described which must subsequently be reduced in a reducing atmosphere at high temperature to obtain the desired copper metal phase ($Cu^0$). It is understood that the extra cost in terms of energy required for the reduction process, the cost of hydrogen and engineering in general, make the whole catalyst preparation procedure a process that is not entirely efficient.

Contrary to such works, the Applicant, through its innovative confinement of the active phase inside the mesoporous silica pores, has succeeded in obtaining the copper-based metal powder directly by operating a self-combustion in static air, which does not has predicted the use of the most expensive argon gas.

The process for the preparation of the catalyst, led to the preparation of a material, which shows, under the same operating conditions, catalytic performances in terms of methanol productivity and/or, especially, selectivity much higher than the results known in the literature (see comparison of Table 4 with the values of $Y_{CH3OH}$ and $S_{CH3OH}$ (%) in the cited prior art documents and see also Table 5).

The Applicant has been able to obtain, unlike the few works cited in the literature on supported catalysts, directly the desired metallic copper phase, calcining, unlike the methods reported in the literature, directly in a static atmosphere of air; moreover, this phase remains stable in an air atmosphere even after months of its preparation.

As a result, the prepared material has been successfully used as such in the catalytic hydrogenation reaction of the $CO_2$ to produce methanol without any activation treatment (see entry 2 of table 6).

Particle size, surface area and catalyst composition are important factors influencing activity and selectivity to give methanol. These factors are in turn influenced by the different methods of preparation.

The preparation process allows to obtain copper and metal oxides powders highly crystalline, homogeneous and of high purity.

From the comparison of the two composites CZS_20_1 and CZZS_20_1, with the same active phase loading (20 w/w %) and the Cu/Zn ratio (≈1), it is possible to highlight the clear superiority of the catalyst in which it is present zirconia, showing a more than doubled methanol productivity (158 mg versus 376 mg $CH_3OH*h^{-1}$ $g^{-1}$ respectively; see table 4).

Last important result is that obtained from the catalytic comparison test on the most active catalyst, with and without activation treatment. It has been experimentally established that the catalyst that has not undergone reductive treatment in a reducing atmosphere works even better than the activated one (see example 9).

From the analysis of the results what has emerged is the fact that the two catalysts work similarly in terms of $CO_2$ conversion (450 versus 376 mg $CH_3OH*h^{-1}$ $g^{-1}$ respectively), but the catalyst without activation treatment shows a selectivity towards methanol which is about 6% higher.

As mentioned, from an industrial point of view the catalytic hydrogenation processes, including that for the synthesis of methanol, must necessarily provide the activation step in the reducing atmosphere of the material in order to be subsequently used as an efficient catalyst in the process. For this reason, catalyst producers usually provide specifications on the activation procedure.

Another object of the invention is the process for the preparation of methanol by catalytic hydrogenation of the carbon dioxide wherein the catalyst used is that described in the previous pages and that obtainable from the above-described process for the preparation of the catalyst.

The catalyst as described above or as obtained from the aforementioned process can therefore be conveniently used for the preparation of methanol.

EXPERIMENTAL SECTION

Example 1

Preparation of mesoporous silica of the SBA-15 type. The synthesis of SBA-15 mesoporous silica was performed according to the original procedure reported by Zhao (Zhao et al., 1998). It consists of the use of Pluronic P123 ($EO_{20}PO_{70}EO_{20}$, $M_{av}$=5800, Aldrich) as surfactant, tetraethoxysilane (TEOS, Aldrich) and a 2M solution of HCl in molar ratio. The only difference from the original procedure was the variation in the temperature of hydrothermal treatment; this, in a second preparation, has been raised to 140° C., with the objective of obtaining larger pores.

Pluronic polymer P123 (4 g) was dissolved in 30 g of distilled water and 120 g of 2M solution of HCl, maintaining the solution for 16 hours under vigorous stirring in an flask placed inside an ethylene glycol bath at a controlled temperature of 36° C. After this phase, during which the templating agent forms a transparent stable micellar solution, TEOS (8.5 g) was added drop by drop. The solution is transformed into a milky white suspension, which is left under stirring at 36° C. for 24 hours to allow the hydrolysis and condensation of the TEOS. The suspension obtained was transferred to a Teflon autoclave and placed in an oven at a temperature of 140° C. for 24 hours (in the second preparation, at 100° C. for obtaining the SBA-15 with a pore diameter of 6.7 nm). After vacuum filtration (carried out with the help of Whatmann filters n.5) and washing the solid product with distilled water (3 L), the white obtained solid was dried in a stove overnight at a temperature about 35° C. The complete removal of the templating agent was carried out by calcining in air, slowly increasing the temperature with a rise rate of 5° C./min up to the temperature of 500° C., with an isotherm of 6 hours. A very fine powder of SBA-15 was thus obtained which is named SBA-15_T140.

The diameter of the channels is about 8-9 nm (according to the BJH results shown below) and the wall thickness is about 4 nm.

The surface area was calculated with the BET method; it is resulted to be equal to $S_{BET}$=500 $m^2$/g. For the calculation of the diameter of the mesopores, the BJH method was applied (Barrett, Joyner, Halenda); it is a mathematical process that, taking advantage of the Kelvin equation (which relates the pore diameter with the P/Po pressure inside it), allows to obtain a distribution of the pore diameters from the analysis of the desorption branch of the isotherm. The average diameter $D_p$ resulted to be equal to 8.2 nm. The porous volume was found to be equal to $V_p$=1.23 $cm^3$/g;

In another experiment, performed to the letter as the one just described but by performing the hydrothermal treatment at 100° C., in place of 140° C., SBA-15 with a pore diameter of 6.7 nm was obtained. The SBA-15 thus obtained was named SBA-15_T100.

The characteristics of the two SBA-15 prepared with the 2 experiments are reported.

TABLE 2

Results of the $N_2$ physisorption analysis at −196° C. of the SBA-15 support prepared at 140° C. (SBA-15_T140) and 100° C. (SBA-15-T100).

| Sample | $S_{BET}$ (m$^2$/g) | $D_p$ (nm) | $V_p$ (cm$^3$/g) |
|---|---|---|---|
| SBA-15_T140 | 500 | 8.2 | 1.23 |
| SBA-15_T100 | 700 | 6.7 | 1.20 |

Example 2

Preparation of the catalyst named CZZS_20_2.5 of formula $(Cu)_{0.5}(ZnO)_{0.2}(ZrO_2)_{0.3}$@SBA-15 with final loading of 20 wt. %.

In a 250 cm$^3$ flask appropriately equipped with a thermometer and digital pHmeter (Mettler Toledo SevenExcellence), fixed and placed on top of a heating plate with magnetic stirring, 3.2 g of mesostructured siliceous support (named SBA-15_T100 prepared in example 1), previously dehydrated in an oven at a temperature of 100° C. for at least two hours, are loaded. Subsequently, 32 cm$^3$ of the impregnation solution, containing $Cu(NO_3)_2.3H_2O$ (Aldrich, 99%, 4.3 mmol), $Zn(NO_3)_2.6H_2O$ (Aldrich, 98%, 1.7 mmol), $Zr(NO_3)_4.5H_2O$ (Aldrich, 99%, 2.6 mmol) and glycine (Aldrich, ≥98%, 12.4 mmol) are introduced into the flask drop by drop with the aid of a 50±0.01 cm$^3$ burette, all under vigorous stirring (about 700 rpm) at room temperature. The light blue color impregnation solution has a pH of about 2.50±0.01. The pH of all impregnation solutions is not corrected with any basifying agent but is maintained at spontaneous pH. The molar ratio of metals (Cu(II)+Zn(II)+Zr(IV)) and glycine is fixed at 1:1.44. The corresponding equivalence ratio was 0.69. The final dispersion which is formed once the entire volume of the impregnating solution has been introduced has a light blue color (due to the effect due to the siliceous support of white color). The dispersion is subjected to a brief ultrasonic treatment for about 2-3 minutes to further promote the dispersion and homogenization of the solution along the entire volume of powder, and subsequently, keeping it under continuous stirring, is heated to a temperature between 120 and 150° C., and the water is allowed to evaporate. This is also evidenced by the evolution of abundant white fumes on the outside of the flask and by the increase in viscosity of the dispersion with the consequent transition to the state of "pseudo-gel", i.e. a "gel or jelly-like material", all in a about 60-90 minutes. Afterwards, the gel is transferred into the preheated oven (Nabertherm L5/11/C450) at a temperature of 300° C. in static air for a period of time equal to 90 minutes, for its transformation into the final product. The use of the oven, unlike the heating plate, allows the self-combustion process to be triggered at a uniform temperature along the entire volume of the gel and allows to perform experiments with a high degree of repeatability. The temperature of 300° C. triggers the combustion mechanism leading to the decomposition of the metal nitrates and their conversion to the metallic and oxide phases, generating as a result of this treatment a completely dry powder of "olive green" color.

Example 3

Preparation of the catalyst named CZZS_35_2.5 of formula $(Cu)_{0.5}(ZnO)_{0.2}(ZrO_2)_{0.3}$@SBA-15 with final loading of 35% (w/w %).

In a 250 cm$^3$ flask appropriately equipped with a thermometer and digital pHmeter (Mettler Toledo SevenExcellence), fixed and placed on top of a heating plate with magnetic stirring, 2.6 g of mesostructured siliceous support (called SBA-15_T100 prepared in example 2), previously dehydrated in an oven at a temperature of 100° C. for at least two hours, are loaded. Subsequently, 26 cm$^3$ of the impregnation solution, containing $Cu(NO_3)_2.3H_2O$ (Aldrich, 99%, 7.5 mmol), $Zn(NO_3)_2.6H_2O$ (Aldrich, 98%, 3.0 mmol), $Zr(NO_3)_4.5H_2O$ (Aldrich, 99%, 4.5 mmol) and glycine (Aldrich, ≥98%, 21.7 mmol) are introduced into the flask drop by drop with the aid of a 50±0.01 cm$^3$ burette, all under vigorous stirring (about 700 rpm) at room temperature. The light blue color impregnation solution has a pH of about 2.50±0.01. The pH of all impregnation solutions is not corrected with any basifying agent but is maintained at spontaneous pH. The molar ratio of metals (Cu (II)+Zn (II)+Zr (IV)) and glycine is fixed at 1:1.44. The corresponding equivalence ratio was 0.69. The final dispersion which is formed once the whole volume of the impregnating solution has been introduced has a light blue color (due to the effect due to the siliceous support of white color). The dispersion is subjected to a short ultrasonic treatment for about 2-3 minutes to further promote the dispersion and homogenization of the solution along the entire volume of powder, and thereafter, keeping it continuously under continuous stirring, is heated to a temperature of between 120 and 150° C., and the water allowed to evaporate. This is also evidenced by the evolution of abundant white fumes on the outside of the flask and by the increase in viscosity of the dispersion with the consequent transition to the state of "pseudo-gel", i.e. a "gel or viscous paste", all in a time approximately 60-90 minutes. The gel is then transferred into the preheated oven (Nabertherm L5/11/C450) at a temperature of 300° C. in static air for a period of 90 minutes, for its transformation into the final product. The use of the oven, unlike the heating plate, allows the self-combustion process to be triggered at a uniform temperature along the entire volume of the gel and allows to perform experiments with a high degree of repeatability. The temperature of 300° C. triggers the combustion mechanism leading to the decomposition of the metal nitrates and their conversion to the metallic and oxides phases, generating as a result of this treatment a completely dry powder of "olive green" color.

Example 4

Preparation of the catalyst named CZS_20_1 of formula $(Cu)_{0.5}(ZnO)_{0.5}$@SBA-15 with final loading of 20% (w/w %).

In a 250 cm$^3$ flask appropriately equipped with a thermometer and digital pHmeter (Mettler Toledo SevenExcellence), fixed and positioned above a heating plate with magnetic stirring, 3.2 g of mesostructured siliceous support (called SBA-15_T100 prepared in example 2) previously dehydrated in an oven at a temperature of 100° C. for at least two hours, are loaded. Subsequently, 32 cm$^3$ of the impregnation solution, containing $Cu(NO_3)_2.3H_2O$ (Aldrich, 99%, 4.97 mmol), $Zn(NO_3)_2.6H_2O$ (Aldrich, 98%, 4.97 mmol)

and glycine (Aldrich, ≥98%, 11.03 mmol) are introduced into the flask drop by drop with the aid of a 50±0.01 cm$^3$ burette, all under vigorous stirring (about 700 rpm) at room temperature. The light blue color impregnation solution has a pH of about 2.50±0.01. The pH of all impregnation solutions is not corrected with any basifying agent but is maintained at spontaneous pH. The molar ratio between metals (Cu (II)+Zn (II)) and glycine is fixed at 1:1.11. The corresponding equivalence ratio was 0.90. The final dispersion which is formed once the entire volume of the impregnating solution has been introduced has a light blue color (due to the effect due to the siliceous support of white color). The dispersion is subjected to a brief ultrasonic treatment for about 2-3 minutes to further promote the dispersion and homogenization of the solution along the entire volume of powder, and subsequently, keeping it under continuous stirring, is heated to a temperature between 120 and 150° C., and the water allowed to evaporate. This is also evidenced by the evolution of abundant white fumes on the outside of the flask and by the increase in viscosity of the dispersion with the consequent transition to the state of "pseudo-gel", i.e. a "gel or viscous paste", all in about 60-90 minutes. Afterwards, the gel is transferred into the preheated oven (Nabertherm L5/11/C450) at a temperature of 300° C. in static air for a period of time equal to 90 minutes, for its transformation into the final product. The temperature of 300° C. activates the combustion mechanism leading to the decomposition of the metal nitrates and their conversion to the metallic and oxides phases, generating as a result of this treatment a completely dry powder of light brown-green color.

Example 5

Preparation of the catalyst named CZZS_20_1 (Cu)$_{0.4}$(ZnO)$_{0.3}$(ZrO$_2$)$_{0.3}$@SBA-15 with final loading of 20% (w/w %).

In a 250 cm$^3$ flask appropriately equipped with a thermometer and digital pHmeter (Mettler Toledo SevenExcellence), fixed and positioned above a heating plate with magnetically stirring, 3.2 g of mesostructured siliceous support (called SBA-15_T100 prepared in example 2) previously dehydrated in an oven at a temperature of 100° C. for at least two hours, are loaded. Subsequently, 32 cm$^3$ of the impregnation solution, containing Cu(NO$_3$)$_2$.3H$_2$O (Aldrich, 99%, 3.4 mmol), Zn(NO$_3$)$_2$.6H$_2$O (Aldrich, 98%, 2.6 mmol), Zr(NO$_3$)$_4$.5H$_2$O (Aldrich, 99%, 2.6 mmol) and glycine (Aldrich, ≥98%, 12.4 mmol) are introduced into the flask drop by drop with the aid of a 50±0.01 cm$^3$ burette, all under vigorous stirring (about 700 rpm) at room temperature. The light blue-colored impregnating solution has a pH of about 2.50±0.01. The pH of all impregnation solutions is not corrected with any basifying agent but is maintained at spontaneous pH. The molar ratio of metals (Cu(II)+Zn(II)+Zr(IV)) and glycine is fixed at 1:1.44. The corresponding equivalence ratio was 0.69. The final dispersion which is formed once the entire volume of the impregnating solution has been introduced has a light blue color (due to the effect due to the siliceous support of white color). The dispersion is subjected to a brief ultrasonic treatment for about 2-3 minutes to further promote the dispersion and homogenization of the solution along the entire volume of powder, and subsequently, keeping it under continuous stirring, is heated to a temperature between 120 and 150° C., and the water allowed to evaporate. This is also evidenced by the evolution of abundant white fumes on the outside of the flask and by the increase in viscosity of the dispersion with the consequent transition to the state of "pseudo-gel", i.e. a "gel or viscous paste", all in about 60-90 minutes. Afterwards, the gel is transferred into the preheated oven (Nabertherm L5/11/C450) at a temperature of 300° C. in static air for a period of time equal to 90 minutes, for its transformation into the final product. The temperature of 300° C. triggers the combustion mechanism leading to the decomposition of the metal nitrates and their conversion to the metallic and oxides phases, generating as a result of this treatment a completely dry powder of light green color.

Example 6

Preparation of the catalyst named CZZ_F_T300_pHsp of formula (Cu)$_{0.5}$(ZnO)$_{0.2}$(ZrO$_2$)$_{0.3}$—comparative—not part of the invention.

10 mL of an aqueous solution of copper nitrate (Cu(NO$_3$)$_2$.3H$_2$O, Aldrich, 99%, 10 mmol), zinc nitrate (Zn(NO$_3$)$_2$.6H$_2$O, Aldrich, 98, %, 4.2 mmol), zirconium nitrate (Zr(NO$_3$)$_4$.5H$_2$O, Aldrich, 99%, 6.25 mmol) were prepared in a beaker. In another beaker 10 mL of an aqueous glycine solution (NH$_2$CH$_2$COOH, Aldrich, 99%, 29 mmol) are prepared. The two completely solubilized solutions are mixed together inside a beaker under constant stirring for about 10 minutes. The solution initially has a light blue color with a spontaneous pH value of 1.50±0.01. Also in this case the pH is not corrected with any addition of basifying agent, but the solution is used at the spontaneous pH. The molar ratio of metals (Cu (II)+Zn(II)+Zr (IV)) and glycine is fixed at 1:1.44. The corresponding equivalence ratio was 0.69.

The resulting solution, transferred into a 250 cm$^3$ flask appropriately equipped with a thermometer and digital pHmeter (Mettler Toledo SevenExcellence), fixed and placed on top of a heating plate with magnetic stirring, is evaporated, with a consequent reduction in volume of the liquid, at a temperature of about 120-150° C., until an increase in viscosity is observed, and the consequent transition to the gel state, all in a time of about 50-60 minutes. The gel, firmly adherent to the beaker walls, is transferred inside the preheated oven (Nabertherm L5/11/C450) at a temperature of 300° C. in static air for a period of time equal to 90 minutes, for its transformation into the final product. The temperature of 300° C. activates the combustion mechanism leading to the decomposition of the metal nitrates and their conversion to the metallic and oxides phases, generating as a result of this treatment a completely dry powder of dark brown color with metallic reflections.

An additional experiment on this type of unsupported catalyst was conducted to visually observe the course of the auto-ignition reaction, in which it was decided to conduct the gel ignition directly on the heating plate. The gel, firmly adherent to the beaker walls, is brought to a temperature of 300° C., in which a swelling of the gel is first observed with the consequent development of a large quantity of white fumes (CO$_2$, N$_2$, H$_2$O), followed by real self-combustion. As previously stated, the self-propagating combustion is in fact an oxidative-reductive reaction in which the nitrate ions act as an oxidizing agent while the glycine acts as the reducing agent. The reaction, which occurs without flame, but still very fast, begins in the part of the beaker in contact with the plate (warmer area), causing a rapid transformation of the gel into the final product. During this process, the amorphous precursor is transformed into an ash that is organized into a solid branched structure. The final material, which is dark brown with metallic reflections, is ground in an agate mortar and reduced to powder, to be characterized structurally.

This non-supported catalyst is called Cu/ZnO/ZrO$_2$ (CZZ_F_T300_pHsp).

Example 7

Characterization of Catalysts

The ICP-AES analyzes of the catalysts prepared in Examples 2-6 indicate the total active phase and the ratio of metals is in good agreement with the nominal values.

TABLE 3

Nitrogen physisorption data of the above prepared catalysts compared with silica and an unsupported catalyst (CZZ_F_T300_pHsp).

| Entry | Sample | $S_{BET}$ (m$^2$ g$^{-1}$) | $D_p$ (nm) | $V_p$ (cm$^3$ g$^{-1}$) |
|---|---|---|---|---|
| 1 | SBA-15_T100 | 643 | 6.7 | 1.06 |
| 2 | CZS_20_1 | 447 | 6.5 | 0.81 |
| 3 | CZZS_20_1 | 433 | 6.4 | 0.73 |
| 4 | CZZS_20_2.5 | 441 | 6.4 | 0.74 |
| 5 | CZZS_35_2.5 | 325 | 6.2 | 0.53 |
| 6 | CZZ_F_T300_pHsp | 12 | — | 0.04 |

$S_{BET}$: BET Specific surface area; $V_p$: Pore volume; $D_p$: Diameter of the pores. Standard deviations: % RSD ($S_{BET}$) = 2.1%; % RSD ($V_p$) = 1.1%; % RSD ($D_p$) = 1.8%.

The surface area BET was measured with I BET method.

The pore diameter was calculated with the BJH method, i.e. Barrett, Joyner, Halenda method (E. P. Barret, L. G. Joyner and P. P. Halenda, *J. Am. Chem. Soc.*, 1951, 73, 373).

FIG. 1 shows the well-ordered structure of SBA-15 based catalysts with 2D-hexagonal symmetry with regular mesochannels of about 6-7 nm in diameter and walls having a thickness of about 5 nm. The characterization techniques reveal that the metal phase is highly dispersed inside and above the well-ordered mesoporous channels, especially the low-quantitative metal compared to the substrate (from 15 to 25 w/w %).

In all the catalysts, the mesostructures of the support are maintained, together with high surface area, large pore volume and uniform pore size.

The TEM analysis of the catalyst CZZS_20_1 (FIGS. 1-A, 1-B and 1-C) does not show variations compared to the analysis of the starting SBA-15 silica. No particles of metal oxides are visible on the external surface or inside the pores, but only a slight narrowing of the mesochannels, as also confirmed by the results of the BET analysis.

Example 8

Synthesis of methanol by catalytic hydrogenation of CO$_2$—comparison of supported catalysts on mesostructured silica with unsupported catalysts.

The primary objective of the research line has been focused on the experimental study of methanol production starting from CO$_2$ alone. The reaction of interest is the catalytic conversion with hydrogen:

CO$_2$+3H$_2$→CH$_3$OH+H$_2$O

The "type" experiment described below was carried out exactly in the same way for all the catalysts under study.

The catalytic test is carried out on the automated "Microactivity Efficient, PID Eng & Tech", using a fixed bed reactor made of stainless steel (9.1 mm I.D.×304.8 mm long). The reactor is equipped with a porous septum in Hastelloy C with a pore diameter of 20 μm on which a quartz wool bed is gently placed on which the catalyst bed is "deposited", all within the isothermal zone guaranteed by the manufacturers (which extends for a length of about 5 cm). The catalytic bed consists of 0.45 g of supported catalyst (CZS and CZZS series, the SBA-15 silica constituting the catalyst support also acts as an inert in the hydrogenation reaction) or 0.45 g of non-supported catalyst (CZZ series) suitably diluted with α-Al$_2$O$_3$ thus obtaining a catalytic bed of about 3 cm$^3$. It was decided to load the catalyst in powder form, only after carefully assessing the absence of pressure drops between the inlet and the outlet of the reactor.

The gas supply for the catalytic study consists of an H$_2$/CO$_2$ mixture with the following ratios (75 mol % H$_2$ and 25 mol % CO$_2$, i.e. a molar ratio 3H$_2$:1CO$_2$). As will be seen in the sections below this stoichiometric mixture, a small percentage of nitrogen used as an internal standard has been added for the correct evaluation of the catalytic conversions and the closure of the mass balance.

The catalytic tests were carried out in two ways depending on whether the activation step of the catalyst is incorporated or not.

1) Test with Activation of the Catalyst

Upstream of the catalytic test, all fresh catalysts are activated "in-situ" by reduction with a gaseous stream consisting of 10% v/v of hydrogen in the nitrogen balance at the temperature of 300° C. reached with a ramp of 3° C./min at a temperature of 300° C. with a two-hours isotherm, all at atmospheric pressure. Once the reduction step is completed, the temperature is lowered (in an inert nitrogen atmosphere) to the reaction temperature, i.e. 250° C., at the end of which the reaction mixture is sent (CO$_2$:H$_2$:N$_2$=22.5:67.5:10 v/v, where nitrogen is used as the internal standard for a correct evaluation of gas-chromatographic analyzes) and the system is simultaneously pressurized at the operating pressure of 3.0 MPa (30 bar). The stationary state was evaluated for all catalysts after one hour from the sending of the reaction mixture. The composition and relative concentration of the inlet gases and the gases leaving the reactor have been continuously monitored by an online micro gas chromatograph (SRA R3000) equipped with a thermoconductivity detector (TCD) for the qualitative and quantitative determination of H2, CO$_2$, CO and other possible hydrocarbons that could form as "by-product" (CH$_4$, C$_3$H$_8$, C$_4$H$_{10}$ and other alkanes and alkenes). The part of the condensable products (recovered in the liquid/liquid/gas separator), i.e. methanol and water, were analyzed offline by means of a gas chromatograph coupled with a mass spectrometer (Agilent 7890A coupled with Agilent 5977A MSD) equipped with a PoraPlot Q 25 capillary column meters (0.25 mm, narrowbore).

2) Test without Activation of the Catalyst

Upstream of the catalytic test, all fresh catalysts are "conditioned" in situ, i.e. they are brought directly to the reaction operating conditions. This step is carried out with a flow of nitrogen, bringing the reactor to the reaction temperature of 250° C. with an ascending ramp of 3° C./min, all at atmospheric pressure. To complete this step, the reactive gas (CO$_2$:H$_2$:N$_2$=22.5:67.5:10 v/v, where nitrogen is used as the internal standard for a correct evaluation of gas-chromatographic analyzes) is sent to the reactor (flow rate total volume of 333 Nml min$^{-1}$) and the system is simultaneously pressurized at the operating pressure of 3.0 MPa (30 bar). The remaining steps are totally the same as the previous one.

Hourly productivity of methanol, or the so-called STY (Space Time Yield) indicating the yield in methanol per gram of catalyst per hour (gCH$_3$OH g$_{cat}^{-1}$ h$^{-1}$) has been calculated using the following formula:

STY(CH$_3$OH)=(WTot*X(CH$_3$OH))/(t*m)

where WTot represents the amount of methanol and water formed during the reaction (g), X(CH$_3$OH) is the mass fraction of methanol, t denotes the reaction time (h), m is the catalyst mass (g).

The methanol yield has been calculated as:

$Y_{CH3OH}$ (%)=(moles of CH$_3$OH produced)/(moles of CO$_2$ fed)*100

The selectivity to methanol has been calculated as:

$S_{CH3OH}$ (%)=(moles of CH$_3$OH produced)/(total moles of products)*100

The CO selectivity has been determined as:

$S_{CO}$=(CO/N$_2$)$_{out}$/(CO$_2$/N$_2$)$_{in}$—(CO$_2$/N$_2$)$_{out}$*100

All catalytic tests were conducted three times for each catalyst and the values of standard deviations for STY and selectivity ranged from 2 to 5%.

The conditioning procedure suitable for preheating the entire unit is carried out with inert gas (N$_2$) at atmospheric pressure up to the activation temperature with a temperature ramp of 2-3° C./min. The activation temperature can be varied from time to time according to the results of the analyzes of the reduction at programmed temperature of each individual catalyst. Once the desired temperature has been reached, the reactor is set up for the reduction step with a total flow equal to 270 ml/min and a 15% H$_2$/N$_2$ gas mixture. The next step consists of the pre-reaction, in which the system is brought to the working pressure (preliminary to 30 bar) with a ramp of 5 bar/min with nitrogen gas. Then the H$_2$/CO$_2$ mixture is progressively sent with a 3:1 molar ratio and with a volumetric flow rate of 300 Nml min$^{-1}$. As previously mentioned, a small amount of nitrogen (about 10%) is added to this mixture as an "internal standard" for on-line readings to the gas chromatograph, bringing the total volumetric flow rate to the 333 Nml min$^{-1}$ reactor. This feed corresponds to a GHSV of about 6000 h$^{-1}$ and refers to the entire catalytic bed (i.e. the 3 cm$^3$ occupied by both the active phase and the inert) which also corresponds to 44000 cm$^3$ gcat$^{-1}$ h$^{-1}$. Conventionally, the start of activity (t=0) is matched with the instant in which the catalytic system reaches the reaction conditions (when the temperature and the working pressure are reached). Once the start-up procedures have been completed, the system is in running condition to conduct the catalytic reaction.

The operating conditions that were finally selected to evaluate the catalytic performances for all the catalysts object of the experimental campaign are summarized below:

T=250° C.; P=30 bar; H$_2$/CO$_2$=3 mol mol$^{-1}$; GHSV=6000 h$^{-1}$ or 44000 cm$^3$ gcat$^{-1}$ h$^{-1}$; T.o.S.=variable between 24 and 60 h.

In the following Table 4 the experimental results of the experimental campaign conducted on the "XtL" bench-scale plant concerning the catalysts prepared in the examples 2-5 are summarized. Table 4 shows the final results in terms of hourly mass of methanol obtained per gram of active phase on the catalysts tested (mg CH$_3$OH h$^{-1}$ gcat$^{-1}$) and also the comparison of the different synthesized catalysts (supported and not supported) always in terms of methanol productivity by mass of catalyst.

TABLE 4

Comparative catalytic results - effect of the siliceous support

| # | Catalyst name Composition % (weight metals and oxides)/total weight | $S_{BET}$ (m$^2$ g$^{-1}$) | T.o.S. (h) | $S_{CO}$ (mol %) | $S_{CH3OH}$ (mol %) | mg CH$_3$OH h$^{-1}$ gcat$^{-1}$ | $Y_{CH3OH}$ (%) |
|---|---|---|---|---|---|---|---|
| 1 | CZZ1_F_T300_pHsp (0.45 g) (Cu)$_{0.5}$(ZnO)$_{0.2}$(ZrO$_2$)$_{0.3}$— | — | 51 | 66.69 | 33.31 | 9.97 | 0.155 |
| 2 | CZZS_20_2.5 (0.45 g) (Cu)$_{0.5}$(ZnO)$_{0.2}$(ZrO$_2$)$_{0.3}$@SBA-15, 20% p/p % | 441 | 31 | 73.63 | 26.37 | <u>324.30</u> | <u>5.05</u> |
| 3 | CZZS_20_1 (0.45 g) (Cu)$_{0.4}$(ZnO)$_{0.3}$(ZrO$_2$)$_{0.3}$@SBA-15, 20% p/p % | 433 | 46 | 69.40 | 30.6 | <u>376.12</u> | <u>5.86</u> |
| 4 | CZZS_35_2.5 (0.45 g) (Cu)$_{0.5}$(ZnO)$_{0.2}$(ZrO$_2$)$_{0.3}$@SBA-15, 35% p/p % | 325 | 27 | 75.65 | 24.35 | 250.29 | 3.89 |
| 5 | CZS_20_1 (0.45 g) (Cu)$_{0.5}$(ZnO)$_{0.5}$@SBA-15, 20% p/p % | 447 | 68 | 72.26 | 27.74 | 158.28 | 2.46 |

Reaction conditions: T=250° C.; P=3.0 MPa; H$_2$/CO$_2$=3 mol mol$^{-1}$; GHSV=44,000 cm$^3$ gcat$^{-1}$ h$^{-1}$; W$_{cat}$=0.45 g.

T.o.S. means "Time on stream", i.e. the time when the reaction mixture flows on the catalyst.

With reference to the catalysts formulas of Table 4, for instance CZZS_20_2.5, it means that the catalyst comprises Copper (C), Zinc oxide (Z), Zirconium dioxide (Z); the metal load on the silica is 20% (weight/weight %), and the ratio of the moles of Cu over the moles of ZnO (i.e. Cu/ZnO) is 2.5. Thus a catalyst described by the following formula CZZS_35_2.5, means a catalyst comprising Cu/ZnO/ZrO$_2$, with 35% metal load on the silica (w/w %) and with a Cu/ZnO molar ratio of 2.5. Finally, a catalyst described by the formula CZZS_20_1 means a catalyst comprising Cu/ZnO/ZrO$_2$, with 20% metal load on the silica (w/w %) and with a Cu/ZnO molar ratio of 1.

With reference to the catalysts formulas of Table 4, it is further noted that when mesoporous silica is SBA-15, the catalyst can be described by the following abbreviation: (Cu)$_x$(ZnO)$_y$@SBA-15 or, wherein Zirconium dioxide is also present, by the following: (Cu)$_x$(ZnO)$_y$(ZrO$_2$)$_z$@SBA-15, wherein x, y and z have the meaning discussed above.

From the internal comparison between the supported and non-supported catalysts (from the latter was selected the most promising one, i.e. the one named CZZ1_T300_pHsp) it is possible to deduce some important peculiarities; it can be clearly seen how, under the same operating conditions used (temperature, pressure and GHSV), there is a noticeable effect of the support on the formulation of the catalyst. It is possible to observe that, for the same synthesis method used and chemical composition of the catalyst in terms of quantity of copper, zinc oxide and zirconia, all the supported catalysts are clearly more efficient than the non-supported catalyst. Specifically, the non-supported catalyst CZZ1_F_T300_pHsp, with nominal composition $(CuO)_{0.5}(ZnO)_{0.2}(ZrO_2)_{0.3}$, shows a methanol productivity which is about 32 times lower than the supported counterpart $(CuO)_{0.5}(ZnO)_{0.2}(ZrO_2)_{0.3}$@SBA-15 (9.97 versus 324.30 $mgCH_3OH\ h^{-1}\ gcat^{-1}$, respectively). This result highlights the importance of the mesostructured support on the final catalytic performance of the material. The supported catalyst containing also Zirconium dioxide provides the highest productivity values in terms of methanol.

The non-supported catalyst CZZ1_F_T300_pHsp was analyzed by X-Ray Diffraction. Since there is not the silica support the diffractograms shows clear peaks instead of an almost flat broad band of the spectrum of the supported catalyst. In the XRD diffractogram of the catalyst CZZ1_F_T300_pHsp with nominal composition $(CuO)_{0.5}(ZnO)_{0.2}(ZrO_2)_{0.3}$, all the crystalline reflections (i.e. peaks) are associated with three separated crystalline phase attributed to zincite phase (i.e. ZnO) (by comparison with PDF Card 36-1451), metallic copper (PDF Card 04-836) and tetragonal zirconia phase (i.e. $ZrO_2$) (PDF Card 79-1764). In particular metallic copper shows most intense reflection (i.e. peak) at the $2\theta$=ca. 43.2° (attribution by comparison with the metallic Cu PDF Card 4-0836).

Most importantly, no CuO phase is observed but only metallic Copper is obtained by the process. This finding clearly proves that the process of the invention already provides, at least partially, metallic Copper and not Copper Oxide, which is the reason why the catalyst of the invention do not require the reduction activation step.

Example 9

Synthesis of methanol by catalytic hydrogenation of $CO_2$—comparison of supported catalysts on mesostructured silica with or without activation phase.

With reference to the two procedures described in example 8 which foresee or do not foresee activation step of the catalyst, the catalyst named CZZS_20_1 has been subjected in one case to the activation and in one other not and has therefore been used to produce methanol according to the procedure described above. The following table 6 summarizes the two tests.

TABLE 6

Catalytic results of catalyst CZZS_20_1 with (CZZS_20_1) and without (CZZS_20_1_No act) activation treatment. Reaction conditions: T = 250° C.; P = 3.0 MPa; $H_2/CO_2$ = 3 mol $mol^{-1}$; GHSV = 44,000 $cm^3$ gcat-1 h-1; $W_{cat}$ = 0.45 g.

| Sample | T.o.S. (h) | $S_{CH3OH}$ (mol %) | STY ($mg_{CH3OH}\ h^{-1}\ g_{cat}^{-1}$) | $Y_{CH3OH}$ (%) |
|---|---|---|---|---|
| CZZS_20_1 | 46 | 30.6 | 376 | 5.86 |
| CZZS_20_1_No act | 46 | 36.1 | 450 | 7.01 |

The experimental results show the excellent performance of the composite catalyst CZZS_20_1 even in the absence of the reduction step of activation. This is clear evidence that: (i) the active copper phase is evidently present in the metallic state or (ii) if copper oxide is present it does not affect the overall performance. Surprisingly, it is noted the highest methanol yield per unit of mass of active catalyst without the activation step (450 $mg_{CH3OH}\ h^{-1}\ gcat^{-1}$), being higher than that of the catalyst which has undergone to the reduction treatment of activation (376 $mg_{CH3OH}\ h^{-1}\ gcat^{-1}$). Thus, this comparative experiment confirms not only that the catalysts of the invention do not require the activation phase, but that they perform even better without being subjected to said treatment.

Example 10

Synthesis of methanol by catalytic hydrogenation of $CO_2$—comparison of supported catalysts on mesostructured silica with known catalysts.

In Table 5 are compared the catalytic systems synthesized in the present work, with the same chemical constituents and, tentatively and obviously, under the same operating conditions (considering the importance of the same, in particular temperature and pressure, for productivity in terms of methanol) with the most recent and significant literature data, from which the superior performances of the catalysts of the invention in terms of catalytic efficiency in the production of methanol are shown. In particular, be observed the comparison between them of the catalysts without zirconia and also the comparison between them of the catalysts with zirconia. In both cases, the catalysts of the present work show greater efficiency in the production of methanol.

TABLE 5

Comparison of the catalytic data obtained for the most promising catalyst synthesized by the Applicant with the most significant catalysts reported in the most recent literature.

| n | Catalyst (code) | STY (MeOH) (g/gcat/h) | Cond. (T - P) (° C., bar) | Reference |
|---|---|---|---|---|
| 1 | Cu—ZnO/$Al_2O_3$ | 0.011 | 250 - 20 | Ren et al., 2015 |
| 2 | Cu—ZnO | 0.009 | 250 - 30 | Jeong et al., 2012 |
| 3 | Cu—Zn—Ga | 0.135 | 270 - 30 | Cai et al., 2015 |
| 4 | CuO—ZnO/$Al_2O_3$ | 0.10 0.06 | 250 - 30 | Tursunov et al., 2017 |
| 4 | CuO—ZnO/$SiO_2$ | 0.07 0.05 | 250 - 50 | Tursunov et al., 2017 |
| 5 | CuO—ZnO/$SiO_2$ | 0.06 0.045 | 250 - 30 | Tursunov et al., 2017 |
| 6 | Cu/ZnO-SBA 15 (CZS_20_1) | 0.158 | 250 - 30 | Present work |
| 7 | Cu/ZnO/$ZrO_2$ | 0.210 | 270 - 50 | Dong et al., 2016 |
| 8 | Cu/ZnO/$ZrO_2$-SBA 15 (CZZS_20_1) | 0.376 | 250 - 30 | Present work |

In particular, if reference is made to the supported catalyst CZZS_20_1, which represents the best in terms of catalytic performance between those so far synthesized by the Applicant, it is possible to see from the results reported in Table 5, the best performance in terms of productivity of methanol (STY).

From the comparison it is possible to observe how the catalyst prepared by the Applicant was more active even at relatively lower working pressures (30 bar), compared to the 50 bars required by the CuO—ZnO/$Al_2O_3$ catalyst (O. Tursunov et al., 2017) which, although it is the best, reaches far lower values of productivity of methanol.

Example 11

Further Characterization of the Catalysts

The exposed Copper surface area (abbreviated $S_{Cu}$) has been evaluated by dissociative $N_2O$ adsorption and carried out in a U tube quartz reactor with a thermal conductivity detector (TCD) to monitor the consumption of $H_2$ and expressed as $m^2_{Cu}{}^0/g_{Cu}$ ($S_{Cu}$). $N_2O$ reacts with metallic Cu on the catalyst surface to form $Cu_2O$ and $N_2$ according to the equation (Gervasini et al., 2005):

$$N_2O_{(g)} + 2Cu_{(s)} \rightarrow Cu_2O_{(s)} + N_{2(g)}$$

The used procedure is the following:
1. 0.030 g of fresh catalyst have been first reduced in 5 vol. % $H_2/N_2$ mixture for 1 h at 250° C. with a heating rate of 10° C. $min^{-1}$;
2. Reactive $N_2O$/He gas mixture gas at 40° C. has been passed to ensure complete oxidation of metallic copper to $Cu^+$;
3. Catalyst has been reduced again with a temperature programmed reduction in 5 vol. % $H_2/N_2$ from 40° C. to 400° C. with a heating rate of 10° C. $min^{-1}$.

Copper surface area has been calculated from the amount of $N_2O$ reacted considering a reaction stoichiometry of $N_2O$:Cu of 1:2 and an atomic copper surface density of $1.46 \times 10^{19}$ Cu atoms/$m^2$. The area under the peak of $H_2$, caused by associative desorption of $H_2$ from copper metal surface, is used to determine the copper surface area from the following equation:

$$\text{Cu surface area } (m^2\ g^{-1}) = (A) \times (S) \times (NA)/SD_{Cu}$$

where A is the amount of $H_2$ desorbed from the TPR peak (mol $H_2$ $gcat^{-1}$), S the stoichiometric factor (2), NA is the Avogadro's number ($6.022 \times 10^{23}$ atoms $mol^{-1}$), $SD_{Cu}$ is the copper surface density ($1.46 \times 10^{19}$ Cu atoms/$m^2$).

The Copper surface area ($S_{Cu}$) is expressed as $m^2$ of Copper (0) (i.e. metallic Copper) per gram of Copper (abbreviated $m^2_{Cu}{}^0/g_{Cu}$).

Copper dispersion, abbreviated $D_{Cu}$(%), defined as the amount of $H_2$ desorbed from the TPR peak divided by the total copper atoms present in the catalyst, is calculated by the following equation:

$$\text{Cu dispersion (\%)} = D_{Cu}(\%) = (A) \times (S) \times (MW_{Cu})/\text{Cu content (wt. \%)} \times 100$$

where $MW_{Cu}$ is the molecular weight of atomic copper (63.546 g $mol^{-1}$).

Moreover, mean copper particles size has been determined considering spherical geometry of the particle. Table 7 shows the surface features for the Cu/ZnO/$ZrO_2$@SBA-15 catalysts. Both samples exhibit high values of $Cu^0$ surface area and dispersion, considerably higher than those of the Cu/$SiO_2$ catalysts synthetized through impregnation (Gervasini et al. 2005, Bond et al. 1989).

TABLE 7

Metal properties of Cu/ZnO/$ZrO_2$@SBA-15 catalysts.

| Sample | Cu (wt %) | $D_{Cu}$ (%) | $S_{Cu}$ ($m^2_{Cu}{}^0/g_{Cu}$) | $D_{part.}$ (nm) | $S_{CH3OH}$ (mol %) | $Y_{CH3OH}$ (%) |
|---|---|---|---|---|---|---|
| CZZS_35_2.5 | 11.7 | 26.6 | 171 | 3.9 | 24.35 | 3.89 |
| CZZS_20_1 | 5.0 | 47.2 | 304 | 2.2 | 30.6 | 5.86 |

Table 7 shows significant difference in terms of dispersion $D_{cu}$(%) and metallic surface area $S_{Cu}$ of the catalyst of the invention compared with those of the patent publication CN106076395A.

It is possible to observe the highest copper dispersion of CZZS_35_2.5 and CZZS_20_1 catalysts compared to the catalysts prepared in the CN106076395A patent, even at high active phase loading (CZZS_35_2.5 sample). Metal dispersion shows a descending trend from 47.2% to 26.6% with increasing of the Cu/Zn molar ratio and active phase loading. In particular, the CZZS_20_1 material, showing the best catalytic performance, exhibits a copper dispersion (47.2%) which is more than doubled than that of the corresponding catalysts in said patent publication (22.9%); it confirms the improvement obtained through the innovative impregnation-sol-gel autocombustion of the process of the invention. As shown, metal surface area referred to grams of copper is really high, contributing to the excellent performance exhibited by these catalysts (see the productivity of methanol provided in Table 4, 5, and 6.

Finally, Dpart. in Table 7 is the average particles size of copper particles (3.9 nm and 2.2 nm for CZZS_35_2.5 and CZZS_20_1, respectively) which is in agreement with XRD findings and provides a clear indication that the active phase nanoparticles are located inside the mesopores of the silica matrix (which have diameters comprised between 6 and 9 nm. Thus, the catalyst has average particles size of copper particles comprised between 2.0 nm and 4.0 nm, preferably between 2.5 nm and 2.0 nm. Said average copper particle size has been calculated as: $D_p(nm) = 10^7 \ast SK \ast C_M \ast W_{Cu}/SF \ast Mol_{H2} \ast NA \ast d_{Cu}$, where SK is a constant depending on Cu particle shape (6 or 5), $C_M$ the number of surface copper atoms per unit surface area ($1.46 \ast 10^{19}$ atoms $m^{-2}$), Wcu the Cu content (wt. %), SF the stoichiometric factor (2), $MolH_2$ the moles of hydrogen experimentally consumed per unit mass of catalyst ($\mu mol_{H2}\ g^{-1}_{cat}$) and $d_{Cu}$ is the density of copper (8.92 g $cm^{-3}$). Further details of the method are described in by Gervasini A, et al. in Applied Catalysis A: General (2005); 281; 199-205.

The invention claimed is:

1. Catalyst for the preparation of methanol by catalytic hydrogenation of carbon dioxide, the catalyst comprising:
   copper, zinc oxide and zirconium dioxide;
   supported over a support of SBA-15 mesoporous silica, the catalyst comprising the following composition (I):

$$(Cu)x(ZnO)y(ZrO_2)z \qquad (I)$$

wherein:
   x is between 0.4 and 0.5,
   y is between 0.2 and 0.3, and
   z is 0.3.

2. The catalyst according to claim 1, wherein the mesoporous silica is amorphous silica, has mesoporous structure and a pore diameter between 6 nm and 9 nm.

3. The catalyst according to claim 1, having a surface area between 300 $m^2$/g and 500 $m^2$/g.

4. The catalyst according to claim 3, having a surface area between 400 and 480 $m^2$/g.

5. The catalyst according to claim 1, having a copper surface area between 100 $m^2$ and 400 $m^2$ of copper (0) per gram of copper.

6. The catalyst according to claim 5, having a Copper surface area between 150 $m^2$ and 350 $m^2$ of copper (0) per gram of copper.

7. The catalyst according to claim 1, having a copper dispersion between 25% and 50%.

8. The catalyst according to claim 7, having a copper dispersion between 40% and 50%.

9. The catalyst according to claim 1, having a pore volume between 0.5 cm$^3$/g and 0.9 cm$^3$/g.

10. The catalyst according to claim 1, having a pore diameter between 6.2 nm and 6.5 nm.

11. The catalyst according to claim 1, wherein the ratio between the sum of the weight of the Cu, ZnO and ZrO$_2$ and the weight of the mesostructured silica is between 15% and 25% (w/w %).

12. The catalyst according to claim 1, wherein x is 0.5, y is 0.2 and z is 0.3; or wherein x is 0.4, y is 0.3 and z is 0.3.

13. Process for synthesizing the catalyst of claim 1 for the preparation of methanol by means of catalytic hydrogenation of carbon dioxide comprising:
    said process comprising the following steps:
    a) preparing an aqueous solution comprising a complexing agent and a copper salt, a zinc salt and a zirconium salt;
    b) mixing of the support of mesoporous silica with the solution of the step a);
    c) forming a gel;
    d) triggering a self-combustive process of the gel and a self-combustive step; and
    e) obtaining the catalyst.

14. The process according to claim 13, wherein the ratio of moles of the complexing agent and the sum of the moles of the copper, zinc and zirconium is between 1.1 and 1.7.

15. The process according to claim 13, wherein the complexing agent is glycine and copper, zinc and zirconium salts are nitrates salts.

16. The process according to claim 13, wherein step d) is carried out at a temperature between 100° C. and 150° C.

17. The process according to claim 13, wherein step e) is carried out at a temperature between 270° C. and 330° C.

18. Catalyst for the preparation of methanol by catalytic hydrogenation of carbon dioxide comprising:
    copper, zinc oxide and zirconium dioxide;
    supported over a support of SBA-15 mesoporous silica said catalyst comprising the following formula of $(Cu)_x(ZnO)_y(ZrO_2)_z$, wherein x is between 0.4 and 0.5, y is between 0.2 and 0.3, and z is 0.3;
    said catalyst obtainable by a process comprising:
    a) preparing an aqueous solution comprising a complexing agent and a copper salt and a zinc salt, or a copper salt, a zinc salt and a zirconium salt;
    b) mixing of the support of mesoporous silica with the solution of the step a);
    c) forming a gel;
    d) triggering a self-combustive process of the gel and a self-combustive step; and
    e) obtaining the catalyst.

* * * * *